United States Patent
Wu et al.

(10) Patent No.: US 9,032,821 B2
(45) Date of Patent: May 19, 2015

(54) ARTICLES FOR SCREENING INSECT PEST-REPELLENTS AND USES THEREOF

(71) Applicant: National Taiwan University, Taipei (TW)

(72) Inventors: Wen-Jer Wu, Taipei (TW); Rong-Nan Huang, Taipei (TW); Li-Chong Su, Taipei (TW)

(73) Assignee: National Taiwan University, Taipei (TW)

( * ) Notice: Subject to any disclaimer, the term of this patent is extended or adjusted under 35 U.S.C. 154(b) by 423 days.

(21) Appl. No.: 13/626,888

(22) Filed: Sep. 26, 2012

(65) Prior Publication Data

US 2014/0083214 A1    Mar. 27, 2014

(51) Int. Cl.
| | |
|---|---|
| *G01N 33/50* | (2006.01) |
| *A01N 65/00* | (2009.01) |
| *G01N 33/52* | (2006.01) |
| *A01N 25/00* | (2006.01) |
| *A01N 37/18* | (2006.01) |
| *A01N 65/44* | (2009.01) |
| *A01N 65/24* | (2009.01) |
| *A01N 65/28* | (2009.01) |
| *A01N 25/34* | (2006.01) |
| *A01N 65/36* | (2009.01) |

(52) U.S. Cl.
CPC ............ *G01N 33/5085* (2013.01); *A01N 65/00* (2013.01); *G01N 33/528* (2013.01); *A01N 25/00* (2013.01); *A01N 37/18* (2013.01); *A01N 65/44* (2013.01); *A01N 65/24* (2013.01); *G01N 2333/43552* (2013.01); *A01N 65/28* (2013.01); *A01N 25/34* (2013.01); *A01N 65/36* (2013.01)

(58) Field of Classification Search
CPC ............ G01N 33/5085; G01N 33/528; G01N 2333/43552; A01N 25/00; A01N 25/34; A01N 65/24; A01N 65/36; A01N 65/00; A01N 65/28; A01N 65/44; A01N 37/18
USPC .......................................................... 73/866
See application file for complete search history.

(56) References Cited

U.S. PATENT DOCUMENTS

| | | | |
|---|---|---|---|
| 3,080,275 A * | 3/1963 | Grady et al. .................. | 514/714 |
| 3,808,339 A * | 4/1974 | Bordenca ........................ | 14/659 |
| 2005/0208157 A1* | 9/2005 | Navarro et al. ............... | 424/756 |

* cited by examiner

*Primary Examiner* — John Fitzgerald
*Assistant Examiner* — Marrit Eyassu
(74) *Attorney, Agent, or Firm* — Chih Feng Yeh; Huntington IP Consulting Co., Ltd.

(57) ABSTRACT

Disclosed herein are improved articles for screening candidate insect pest-repellents; and their uses in host-free methods and/or systems for screening candidate insect pest-repellents.

13 Claims, 2 Drawing Sheets

ARTICLES FOR SCREENING INSECT PEST-REPELLENTS AND USES THEREOF

BACKGROUND ART

1. Technical Field

The present disclosure relates to an article for screening candidate insect repellents, and uses thereof.

2. Description of Related Art

Insect pests, particularly those live by hematophagy on the blood of other animals, such as mammals, birds, reptiles and amphibians, are nuisance to their hosts, and sometimes are responsible for transmitting diseases. For example, fleas are responsible for transmitting the majority of vector-borne zoonosis diseases, such as plague, murine typhus, tapeworm, and cat scratch disease. Bites made by such pests often causes itching sensation, which in turn may result in the host attempting to ease the itching sensation by biting, pecking, scratching, etc. in the vicinity of the bites; in more severe cases, host will develop rashes due to allergy reaction to the saliva of such insect pest. Hence, the prevention of pest bites and the prompt detection and removal of attached pests may greatly reduce the chance of developing allergy reactions and/or vector-borne diseases. Wearing a repellent can substantially increase the level of protection or reduce the chance of being attacked by such pests. A variety of repellent assays have thus been developed for evaluating candidate substances or formulations. In general, these tests can be classified into two categories: use of live hosts with or without some sort of attractants associated with hosts, or no use of live hosts at all. The latter is better to standardize and is cheap, but suffers from a poor ability to filter out weak repellents. The former is usually more predicative in forecasting the efficacy of the substance under certain conditions, though sometimes difficult to standardize, particularly in the field, and is usually more expensive and time-consuming.

In view of the forgoing problems, there exists in this art a need to develop an improved insect pest repellent assay that is not only simple, fast, and cheap; but also can be reproduced in mass numbers to speed up the screening process when thousands of candidate compounds are involved, and with an improved ability to filter out weak repellents.

SUMMARY

In view of the afore-mentioned problem, an article for screening a candidate insect pest-repellent, and a method of using the same are disclosed.

Thus, it is the first objective of the present invention to provide an article for screening a candidate insect pest-repellent. The article is composed of a first and second paper strips, respectively having a first and second tapered end. The first and second paper strips are adhered to one another at a small overlapping portion on one of their respective sides along the longitudinal direction with the two tapered ends are disposed side by side and thereby forming the article.

According to embodiments of the present disclosure, both the first and the second paper strips are made of filter papers, and respectively have a size in which the width:length is between about 1:7 and 1:10. To form the article, the first and second paper strips are held together by overlapping a portion of the first and second paper strips along one side in longitudinal direction, and then the overlapping portions are glued together via an adhesive. In one example, the overlapping portion has a size that is about one tenth of the respective size of the first and second paper strips.

The second objective of the present invention is to provide a host-free method of screening a candidate insect pest-repellent using the article of this invention. The method includes the following steps. The candidate insect pest-repellent and a buffer solution are respectively applied onto the first and second paper strips of the article of this invention. The article is then placed in a vertically situated, round-ended tube by allowing the two tapered ends of the first and the second paper strips to be at the bottom of the round-ended tube, where a number of insect pests are placed. The round-ended tube is then sealed, such as by plugging its opening with cottons or sealing it with paraffin. The insect pests are allowed a length of time to climb up the article; then the respective numbers of the insect pests on the first and second paper strips are counted. Repellency (PR %) of the candidate insect pest-repellent is calculated in accordance with the following equation, $$PR\% = \frac{(NC-NT)}{(NC+NT)} \times 100$$

in which NT and NC respectively represent the number of insect pest on the first and second paper strips (i.e., the candidate insect pest-repellent treated and un-treated paper strips, respectively).

According to embodiments of the present disclosure, the round-ended tube has a concave bottom; and the insect pests are allowed to climb up the article for at least 30 min. In one preferred example, the candidate insect pest-repellent is cinnamaldehyde extracted from *Cinnamomum osmophloeum*, with a repellency of at least 97% at a concentration of about 1% (wt %). The method of the present disclosure, when in practice, does not require a live host.

The third aspect of objective of the present invention is to provide a kit for screening a candidate insect pest-repellent. The kit includes the article of this invention; a round-ended tube; and an instruction of how to use the kit, in which the article of this invention is to be placed inside the round-ended tube, with the tapered end of the article of this invention are placed toward the round-end bottom of the tube.

These and other features, aspects, and advantages of the present disclosure will become better understood with reference to the following description and appended claims.

BRIEF DESCRIPTION OF THE DRAWINGS

These and other features, aspects and advantages of the present invention will become better understood with reference to the following description, appended claims and the accompanying drawings, where:

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The singular forms "a", "and", and "the" are used herein to include plural referents unless the context clearly dictates otherwise.

The term "insect pests" as used herein refers to insects live by hematophagy on the blood of other animals such as mammals, birds, reptiles or amphibians. The insect pests include, but are not limited to, fleas, ticks, or mites.

Described herein is an article for screening a candidate insect pest-repellent; and a method of using the same.

Figure 1:
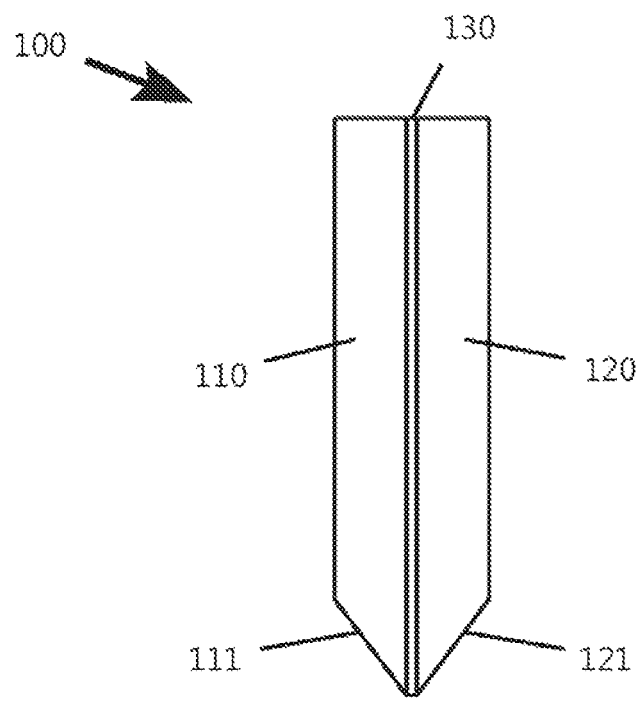
FIG. 1 is a schematic drawing of an article 100 for screening a candidate insect pest-repellent in accordance with one embodiment of the present invention.

Referring to FIG. 1, which is a schematic drawing of an article 100 for screening a candidate insect pest-repellent in accordance with one embodiment of the present invention. The article 100 is composed of a first and second paper strips (110, 120), respectively having a first and second tapered ends (111, 121); and an overlapping portion 130, where the first and second paper strips joined.

Figure 2:
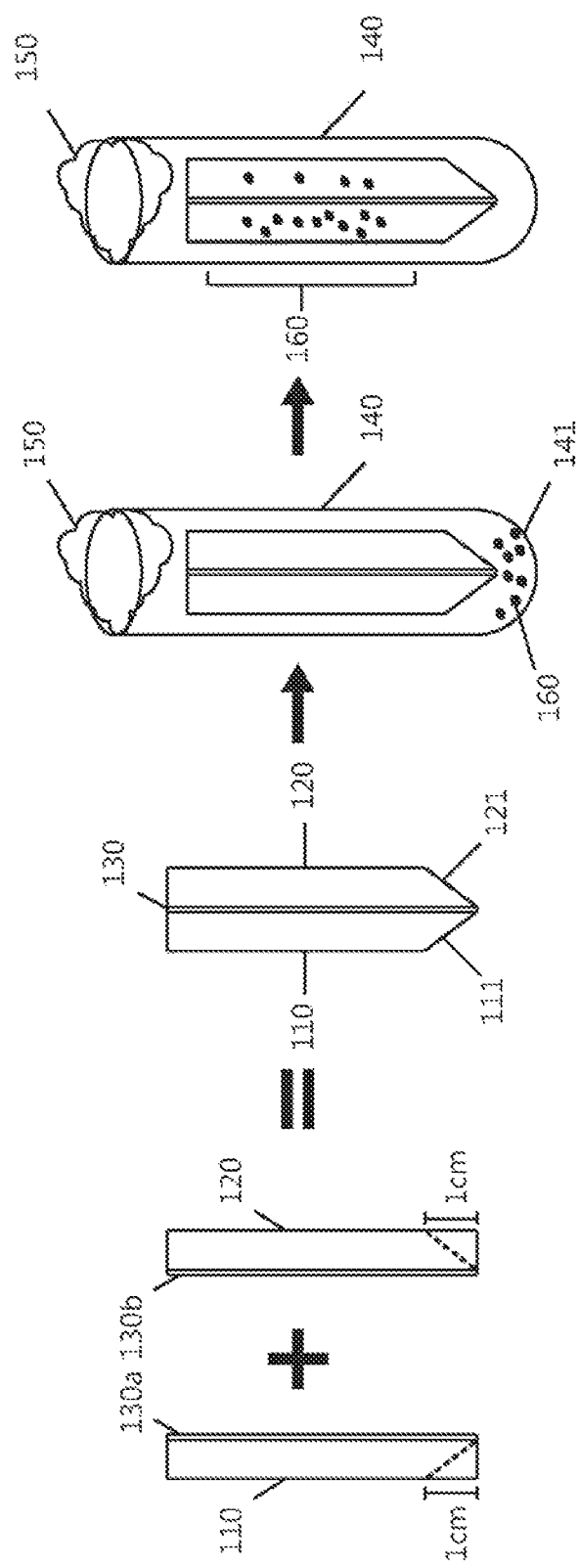
FIG. 2 is a schematic drawing illustrating how the article 100 of FIG. 1 is formed and its application in screening a candidate insect pest-repellent in accordance with one embodiment of the present invention.

FIG. 2 is a schematic drawing of how the article 100 of FIG. 1 is assembled and subsequently used in screening a candidate insect pest-repellent in accordance with one embodiment of the present invention. To form the article 100, two pieces of filter paper strips (110, 120) respectively having a width: length ratio from about 1:7 to 1:10, such as 1:7, 1:8, 1:9 and 1:10, are used. In one example, each paper strip is about 1 cm in width, and 9 cm in length. Each paper strip (110, 120) is cut off diagonally at one end and thereby creates a tapered end (111, 121), while the other end of the paper strip remains blunt. The two paper strips (110, 120) respectively having a tapered end (111, 121) are then joined together by overlapping a small portion of one side (130a, 130b) of the respective strips (110, 120), and the overlapped portions (130a, 130b) are then held together with the aid of an adhesive, such as a glue. Therefore, the thus formed article 100 has a tapered end jointly formed by the two tapered ends (111, 121) of the first and second paper strips (110, 120). In one preferred example, the width of each overlapped portion is about 1/10 of that of the first or second paper strip (110, 120), whereas the length remains relatively the same. Hence, each overlapped portions (130a, 130b) of the first and second paper strips (110, 120) have a size that is about 1/10 of that of the first or second paper strip (110, 120).

In another aspect, a method of screening a candidate insect pest-repellent using the article 100 of FIG. 1 is provided. Referring again to FIG. 2, during the operation of screening an effective insect pest-repellent, a few drops of a candidate insect pest-repellent solution and a control solution (e.g., a buffer or water) are respectively applied onto the two paper strips (i.e., the first and second paper strips (110, 120) respectively having the first and second tapered ends (111, 121)), and allowed them to spread evenly throughout the respective papers. The two paper strips (110, 120) are then let standing for a few minutes to dry. After drying, the two paper strips (110, 120) are placed side by side with a portion (130a or 130b) of one strip underneath a portion (130a or 130b) of the other strip thereby create an overlapped portion (130) along the longitudinal direction of the two paper stripes (110, 120). The two overlapped portions (130a, 130b) are then held together via means such as an adhesive or staples to form the article 100 of FIG. 1. The thus formed article 100 is then placed in a round-end tube 140, with its tapered end being disposed at the bottom 141 of the round-ended tube 140, where a number of insect pests 160 (such as fleas or ticks) have already been placed therein. The round-end tube 140 may be any test tube regularly employed in a chemical laboratory, and is preferably the one with a bottom area of less than 2 cm$^2$, such as 1.5 cm$^2$. The tube 140 is then sealed, such as by paraffin or by plugging its opening with cottons. During operation, the tube 140 is set up in vertical direction for a period of time, for example, at least 30, 40, 50 or 60 min, so that the insect pest have sufficient time to climb up the respective paper strips. In one example, the entire set up (i.e., including the article 100, the tube 140 and the fleas) is let stand for at least 30 min, before the number of insect pests on respective paper strips (110, 120) are counted. Repellency (PR %) of the candidate insect pest-repellent is determined by the following equation, $$PR\ \% = \frac{(NC - NT)}{(NC + NT)} \times 100$$

in which NT and NC respectively represent the number of fleas on the candidate flea-repellant treated and un-treated paper strips, respectively.

According to one embodiment of the present invention, the candidate insect pest-repellent is cinnamaldehyde extracted from *C. osmophloeum*. In this example, the cinnamaldehyde has a repellency of at least 97% at a concentration of about 1% (wt %).

The present method improves the conventional petri-dish method and the vertical tube method by having an article made of two tapered filter papers, and placing the insect pests and the two tapered filter papers respectively treated with the candidate insect pest-repellent and a control buffer solution in a round-ended tube, so that the insect pest at the bottom of the round-ended tube have no place to rest but to choose a preferred area (i.e., area treated with or without the candidate insect pest-repellent) to climb up, and thereby allows a candidate insect pest-repellent to be better differentiated from a non-repellent. Further, the article of the present invention is cheap and easy to assemble, thus can be mass produced and applied in a mass screening procedure for screening thousands of candidate compounds at a relatively low cost, with each screening step capable of being completed within 30 min.

The present invention will now be described more specifically with reference to the following embodiments, which are provided for the purpose of demonstration rather than limitation.

EXAMPLES

Example 1

Developing an Improved Screening System of the Present Invention

In this example, we demonstrated how the article of this invention, and an improved system for screening candidate insect pest-repellents using the article, were developed.

Two types of filter paper articles were constructed. Specifically, article with two blunt ends (herein after "blunt-end article") and article with one tapered end and one blunt end (herein after "tapered-end article"), were constructed in accordance with the procedures depicted in FIG. 2, except minor modifications for the blunt-end article, in which each of the two filter paper stripes were not cut diagonally from one end, and therefore both ends remained blunt after the two filter paper stripes were adhered. Repellents test were then conducted using the respective articles so as to develop an improved system and/or method for screening a candidate insect pest-repellent.

The blunt-end article and the tapered end article were constructed as described above and placed respectively in an inverted centrifuge tube (about 50 ml in volume, hence both blunt ends of the blunt-end article were situated at a flat surface) and a round-ended glass tube (about 36 ml in volume, hence the tapered end of the tapered-end article is disposed on the concave surface of the rounded end). An aliquot of a test repellent (e.g., 0.1 ml of 75% ethanol, or Dr. Mini® (which contains citronella oil, mint, an extract from eucalyptus and etc. as its active ingredients), or OFF® (which contains 15% N,N-Diethyl-meta-toluamid (DEET) as its active ingredient)) was evenly dripped onto one side of the article, and let stand for 30 min until the paper was dried; whereas the other side of the article remained untreated. 20 fleas were then placed inside each tube (i.e., the inverted centrifuge tube or the round-ended glass tube), after 30 min, respective numbers of fleas on each side of the article, as well as in the bottom of the tube were counted. Results are summarized in Table 1.

TABLE 1

|  | Test # | 75% Ethanol | | | Dr. Mini ® | | | OFF ® | | |
|---|---|---|---|---|---|---|---|---|---|---|
|  |  | Treated | Control | Bottom | Treated | Control | Bottom | Treated | Control | Bottom |
| Blunt end article + Flat surface Tube | 1 | 6 | 10 | 4 | 3 | 9 | 8 | 0 | 13 | 7 |
|  | 2 | 10 | 8 | 2 | 3 | 10 | 7 | 0 | 8 | 12 |
|  | 3 | 11 | 6 | 3 | 0 | 16 | 4 | 0 | 19 | 1 |
| Tapered end article + Concave surface Tube | 1 | 8 | 11 | 2 | 3 | 15 | 2 | 0 | 19 | 1 |
|  | 2 | 9 | 9 | 2 | 2 | 17 | 1 | 0 | 18 | 2 |
|  | 3 | 11 | 9 | 0 | 1 | 19 | 0 | 2 | 15 | 3 |

It is evident from the data summarized in Table 1, 75% ethanol possesses no repellent activity towards fleas as compared to the results conducted with the other two commercial available flea repellents; further, the number of fleas remained at the bottom of the tube is much higher in the case when a flat-bottom tube and a blunt-ended article were provided. Taken together, the data suggested that adopting a concave bottom in the tube or having a tapered end in the filter paper article would encourage the climbing-up nature of fleas, and therefore prompting the fleas to choose a preferred filter paper surface (treated vs non-treated) to stay on; hence, improves the differentiating ability of a screening system.

Example 2

Screening Candidate Flea-Repellents by Use of the Screening System of Example 1

The improved system of Example 1, which includes a filter paper article having tapered ends and a tube having a concaved bottom surface was employed in this example for screening a candidate insect pest-repellent from 12 kinds of essential oils respectively extracted from plants of various families, including Rutaceae, Taxodiaceae, Cueculida, Lauraceae, Chenopodiaceae, and Labiatae.

Briefly, each essential oil was diluted with 95% ethanol, and tested at a final concentration of 2%, 1%, 0.5%, 0.25% or 0.125%. 80 µl of a candidate oil was evenly applied onto one side of the filtered paper article, whereas same volume of 95% ethanol was evenly applied onto the other side of the filtered paper. The article was let stand for about 30 min until it was dried. Then, the filtered paper article was placed into a round-ended test tube, which was set up vertically, with the tapered ends facing toward the concaved bottom of the tube. About 30 fleas were then placed into the tube. After 30 min, the numbers of fleas on respective sides of the filtered paper article was then counted. Repellency (PR %) of each candidate essential oils was calculated in accordance with the following equation, $$PR \% = \frac{(NC - NT)}{(NC + NT)} \times 100$$

in which NT and NC respectively represent the number of flees on the candidate essential oil-treated and un-treated paper strips. Results are summarized in Table 2.

TABLE 2

| Plant Family where Essential oils was extracted from | Concentration (wt %) | | | | | |
|---|---|---|---|---|---|---|
|  | 0% | 0.125% | 0.25% | 0.5% | 1% | 2% |
| *Cinnamomum osmophloeum* (Cinnamaldehyde Type) | −5.6 ± 5.2 | 32.5 ± 7.4 | 47.6 ± 0.8 | 68.6 ± 13.6 | 97.7 ± 3.9 | 97.5 ± 4.3 |
| *Cinnamomum osmophloeum* (Linalool Type) | −1.0 ± 8.7 | 10.1 ± 9.0 | 2.9 ± 15.7 | 1.2 ± 19.1 | 3.0 ± 25.3 | 2.2 ± 10.9 |
| *Cinnamomum brevipedunculatum* | −3.6 ± 9.3 | −14.3 ± 22.3 | −4.4 ± 7.6 | −6.9 ± 3.6 | −6.6 ± 13.3 | −1.6 ± 14.6 |
| *Taiwania cryptomerioides* | 2.2 ± 3.8 | −3.0 ± 25.5 | −6.6 ± 6.6 | −3.4 ± 3.3 | 64.2 ± 12.3 | 89.6 ± 9.1 |
| *Cryptomeria japonica* | 7.7 ± 5.0 | −3.5 ± 9.4 | 16.6 ± 14.8 | −3.6 ± 5.7 | 7.0 ± 6.0 | 1.9 ± 14.3 |
| *Cunnighamia konishii* | 0.1 ± 15.5 | −17.0 ± 8.5 | −5.7 ± 2.0 | 2.4 ± 8.5 | −0.2 ± 12.3 | 11.0 ± 10.5 |
| *Citrus taiwanica* | 5.9 ± 7.3 | 4.6 ± 7.1 | −5.5 ± 28.2 | 10.5 ± 10.7 | 12.3 ± 5.3 | 23.8 ± 16.9 |
| *Citrus tachibana* | −1.2 ± 11.3 | −11.3 ± 21.8 | −3.3 ± 8.8 | −7.7 ± 5.0 | −2.3 ± 7.7 | −1.0 ± 10.7 |
| *Clausena excavate* | 1.0 ± 10.7 | 3.6 ± 6.0 | −11.7 ± 7.6 | 0.0 ± 10.3 | 2.2 ± 8.7 | −4.4 ± 7.2 |
| *Gaultheria cumingiana* | −0.1 ± 15.5 | 6.6 ± 1.0 | 3.4 ± 8.8 | 11.4 ± 6.9 | −0.3 ± 17.6 | −4.4 ± 10.1 |
| *Plectroanthus amboinicus* | 15.7 ± 7.4 | 11.2 ± 8.3 | −4.9 ± 9.9 | 35.6 ± 2.3 | 69.5 ± 23.9 | 83.8 ± 9.7 |
| *Chenopodium formosanum* | 3.0 ± 14.8 | 4.7 ± 7.4 | 9.7 ± 7.7 | −6.6 ± 17.3 | −1.0 ± 10.5 | −4.8 ± 10.7 |

From the data presented in Table 2, it is evident that essential oils, except those extracted from *Cinnamomum osmophloeum, Taiwania cryptomerioides* or *Plectranthus amboinicus*, have negligible insect pest-repelling efficacy; and for those extracted from *Cinnamomum osmophloeum, Taiwania cryptomerioides* or *Plectranthus amboinicus*, significant repelling effects were observed when the concentration went above 0.5%, such as about 1%; with the best insect pest-repellent activity exhibited by essential oils (cinamaldehyde type) extracted from *Cinnamomum osmophloeum*.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An article for screening a candidate insect pest-repellent comprising,
   a first paper strip having a first tapered end; and
   a second paper strip having a second tapered end;
   wherein the first and the second paper strips are adhered to one another by overlapping a portion of one respective sides along the longitudinal direction of the first and the second paper strips with the two tapered ends being disposed side by side and thereby forming the article.

2. The article of claim 1, wherein the first and second paper strips are both made of filter papers.

3. The article of claim 2, wherein the first and the second paper strips are respectively having a size in which the width:length is about 1:8.

4. The article of claim 3, wherein the portion is about one tenth in size as compared to that of the first or second paper strip.

5. A kit for screening a candidate insect pest-repellent comprising,
   the article of claim 1;
   a rounded end tube having a concave surface at the bottom; and
   an instruction of how to use the kit, in which the article of claim 1 is to be placed inside the round-ended tube, with both the tapered ends of the article of claim 1 are disposed on the concave surface at the bottom of the tube.

6. A host-free method of screening a candidate insect pest-repellent comprising,
   applying the candidate insect pest-repellent on the first paper strip of the article of claim 1;
   applying a buffer solution on the second paper strip of the article of claim 1;
   placing the article of claim 1 in a vertically situated round ended tube by allowing the two tapered ends of the first and the second paper strips to be disposed at the bottom of the round ended tube;
   placing a number of insect pests at the bottom of the round ended tube;
   allowing the insect pests a period of time to climb up the article of claim 1; and
   counting the respective numbers of the insect pests on the first and second paper strips, and repellency (PR %) of the candidate insect pest-repellent is calculated in accordance with the following equation, $$PR\% = \frac{(NC - NT)}{(NC + NT)} \times 100$$

In which NT and NC respectively represent the number of insect pests on the first and second paper strips.

7. The host-free method of claim 6, further comprising the step of sealing the tube.

8. The host-free method of claim 6, wherein the round ended tube has a concave bottom.

9. The host-free method of claim 8 wherein the period of time is at least 30 min.

10. The host-free method of claim 8, wherein the candidate insect pest-repellent is cinnamaldehyde.

11. The host-free method of claim 10, wherein the cinnamaldehyde has a repellency of at least 97% at a concentration of about 1% (wt %).

12. The host-free method of claim 10 wherein the cinnamaldehyde is extracted from *Cinnamomum osmophloeum*.

13. The host-free method of claim 8, wherein the insect pests are fleas or ticks.

\* \* \* \* \*